United States Patent [19]

Sallmann et al.

[11] Patent Number: 5,096,917

[45] Date of Patent: Mar. 17, 1992

[54] SUBSTITUTED INDOLES

[75] Inventors: Alfred Sallmann, Bottmingen; Willy Meyer, Riehen, both of Switzerland

[73] Assignee: Ciba-Geigy Corporation, Ardsley, N.Y.

[21] Appl. No.: 693,101

[22] Filed: Apr. 29, 1991

[30] Foreign Application Priority Data

May 4, 1990 [CH] Switzerland ............... 1510/90

[51] Int. Cl.$^5$ ............... A61K 31/405; C07D 209/04
[52] U.S. Cl. ............... 514/415; 548/510
[58] Field of Search ............... 514/415; 548/510

[56] References Cited

U.S. PATENT DOCUMENTS

| 4,542,224 | 9/1985 | Raue et al. | 548/511 |
| 4,859,692 | 8/1989 | Bernstein et al. | 548/511 |
| 4,918,094 | 4/1990 | Bernstein et al. | 548/511 |

FOREIGN PATENT DOCUMENTS

| 0199543 | 10/1986 | European Pat. Off. | 548/511 |
| 0220066 | 4/1987 | European Pat. Off. | 548/511 |
| 0227241 | 7/1987 | European Pat. Off. | 548/511 |

Primary Examiner—Mary C. Lee
Assistant Examiner—Joseph K. McKane
Attorney, Agent, or Firm—Irving M. Fishman

[57] ABSTRACT

Novel trisubstituted indole compounds of formula

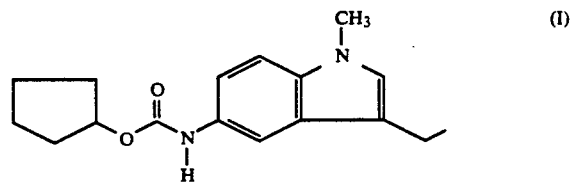

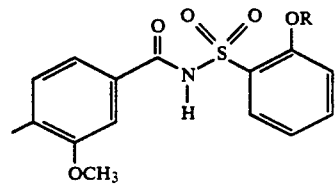

wherein R is straight-chain $C_2$-$C_4$alk-1-en-1-yl, and their salts can be used as pharmaceutical active ingredients and can be manufactured in a manner known per se.

8 Claims, No Drawings

SUBSTITUTED INDOLES

The invention relates to novel trisubstituted indole compounds of formula

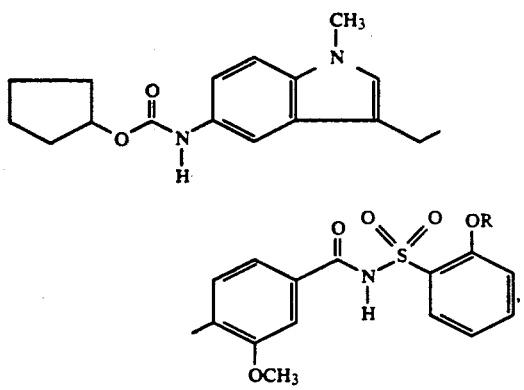

wherein R is straight-chain $C_2$–$C_4$alk-1-en-1-yl, and their salts, to the use of those compounds and salts, to a process for the preparation of those compounds and salts, and to pharmaceutical compositions comprising such a compound I in free form or in the form of a pharmaceutically acceptable salt.

Within the scope of the invention, when the radical R has more than two carbon atoms (C atoms) and therefore can have the (E)- or (Z)-configuration, the compounds I may be in the form of stereoisomers, for example in the form of pure diastereoisomers or mixtures of diastereoisomers. Preference is given within the scope of the invention to compounds I wherein the radical R has the stereochemistry disclosed as examples.

Salts of compounds I are especially pharmaceutically acceptable salts, for example acid addition salts, which are formed, for example, with strong inorganic acids, such as mineral acids, for example sulfuric acid, a phosphoric acid or a hydrohalic acid, with strong organic carboxylic acids, such as lower alkanecarboxylic acids, for example acetic acid, or unsaturated or saturated dicarboxylic acids, for example malonic acid, maleic acid or fumaric acid, or hydroxycarboxylic acids, for example tartaric acid or citric acid, or with sulfonic acids, such as lower alkanesulfonic acids or unsubstituted or substituted benzenesulfonic acids, for example methanesulfonic acid or p-toluenesulfonic acid, or salts with bases, such as suitable alkali metal or alkaline earth metal salts, for example sodium, potassium or magnesium salts, pharmaceutically acceptable transition metal salts, such as zinc or copper salts, or salts with ammonia or organic amines, such as cyclic amines, mono-, di- or tri-lower alkylamines, hydroxy-lower alkylamines, for example mono-, di-or tri-hydroxy-lower alkylamines, hydroxy-lower alkyl-lower alkylamines or polyhydroxy-lower alkylamines. Cyclic amines are, for example, morpholine, thiomorpholine, piperidine or pyrrolidine. Suitable mono-lower alkylamines are, for example, ethylamine and tert-butylamine, suitable di-lower alkylamines are, for example, diethylamine and diisopropylamine, and suitable tri-lower alkylamines are, for example, trimethylamine and triethylamine. Suitable hydroxy-lower alkylamines are, for example, mono-, di- and tri-ethanolamine; hydroxy-lower alkyl-lower alkylamines are, for example, N,N-dimethylaminoethanol and N,N-diethylaminoethanol; and a suitable polyhydroxy-lower alkylamine is, for example, glucosamine.

Also included are salts that are not suitable for pharmaceutical applications, since these can be used, for example, for the isolation and purification, respectively, of free compounds I and of their pharmaceutically acceptable salts.

Hereinbefore and hereinafter, unless indicated otherwise, radicals and compounds designated "lower" are to be understood as being radicals and compounds that have up to and including 7, especially up to and including 4, carbon atoms.

Straight-chain $C_2$–$C_4$alk-1-en-1-yl is vinyl, (Z)-propen-1-yl, (E)-propen-1-yl, (Z)-but-1-en-1-yl or (E)-but-1-en-1-yl.

The compounds I and their pharmaceutically acceptable salts exhibit, for example, valuable pharmacological properties, especially a pronounced leucotriene-antagonism.

For example, in vitro in a concentration range of from approximately 0.001 to approximately 1 μmol/l, they inhibit the contraction of a smooth muscle induced by leucotriene $D_4$ ($LTD_4$). This so-called $LTD_4$-antagonism can be verified experimentally, for example, as follows: in segments which have been removed from the ileum of a guinea pig weighing from 300 to 400 g and which have been incubated in an organ bath in Tyrode's solution at 38° C. while being gassed with a mixture of 95% oxygen and 5% carbon dioxide at a load of 1 g, contractions are induced with synthetic leucotriene $D_4$ (in potassium salt form) and are registered isotonically. The extent of the inhibition of the contractions by the test compound is evaluated as $IC_{50}$ after a preliminary incubation of 2 minutes, $IC_{50}$ denoting the concentration at which the test contractions are reduced by 50%.

The compounds I and their pharmaceutically acceptable salts also have excellent activity in vivo. For example, in a bronchoconstriction standard test on guinea pigs, with administration of an aerosol solution comprising from approximately 0.00001 to approximately 1% by weight of the test compound, a marked $LTD_4$-antagonistic effect can be observed. In this test model, male guinea pigs weighing from 400 to 700 g are anaesthetised intraperitoneally with 1.4 g/kg of urethane, and a polyethylene cannula is inserted into the jugular vein. A second polyethylene cannula is inserted into the trachea. The pressure in the oesophagus is recorded by means of a cannula that is inserted into the oesophagus and that is connected to a Statham pressure transducer. The animal is placed in an airtight plexiglass chamber which is connected to a Fleisch's tube No. 000 and a Validyne transducer MP 45-1. This arrangement is used to measure the flow. After the surgical preparation of the test animals, a certain period of time is allowed to elapse to enable the pulmonary functions to stabilise. The test compound is then administered in accordance with the following procedure. The test animals are exposed for one minute to a 1% (weight/volume) aerosol solution of the test compound or to distilled water (for control purposes). For all the test compounds that are administered by inhalation, a Monaghan ultrasound spray apparatus (model 670) of which the particle size varies between 1 and 8 microns, the majority being 3 microns, is used. Aqueous solutions are freshly prepared each time and are introduced into the chamber of the spray device using an on-stream drug vial. The spray mist produced is administered to the test animals via a glass chamber of 65 ml capacity which is connected to the trachea by a cannula. At the end of the treatment period, LTD$_4$ (0.3 μg/ml) is administered over a period of 2 minutes using a second Monaghan ultrasound spray apparatus (model 670) and via a similar glass chamber. The reduction in compliance is read off in the third minute after the LTD$_4$ administration and the average value of three animals is compared with the average value of three control animals and the percentage inhibition of compliance (% inhibition) is calculated in accordance with the following formula:

$$\% \text{ inhibition} = 100 - \frac{(100 - \text{compliance preparation}) \cdot 100}{(100 - \text{compliance control})}$$

If different concentrations of active ingredient are tested, the percentage inhibition for each concentration is recorded, the "log concentration" on the abscissa being plotted against the "percentage inhibition" on the ordinate. The IC$_{50}$ is then determined by linear regression analysis.

The compounds I and their pharmaceutically acceptable salts also have the specific and therapeutically very significant advantage of a relatively long duration of action.

The compounds I and their pharmaceutically acceptable salts can therefore be used therapeutically in all cases where the action of leucotrienes results in pathological conditions, and alleviate or eliminate these conditions. Leucotrienes play an important part inter alia in the occurrence of allergic and inflammatory processes. Accordingly, the compounds I and their pharmaceutically acceptable salts can be used, for example, as active ingredients in anti-allergic agents which are used, for example, for the treatment of allergic conditions and diseases, such as, especially, asthma, but also hay fever and obstructive pulmonary diseases, including cystic fibrosis. The invention accordingly relates also to the use of the compounds I and their pharmaceutically acceptable salts for the preparation of corresponding medicaments. The commercial formulation of the active ingredients is also included.

Preference is given within the scope of the invention to compounds of formula I wherein R is vinyl, (Z)-propen-1-yl or (E)-propen-1-yl, and their salts.

Special preference is given within the scope of the invention to compounds of formula I wherein R is vinyl or (Z)-propen-1-yl, and their salts.

Very special preference is given within the scope of the invention to the compound of formula I wherein R is vinyl, and its salts.

Within the scope of the invention, preference is given to the compounds of formula I mentioned specifically in the Examples, and their salts.

The present invention relates also to a process for the preparation of compounds of formula I and their salts, which comprises, for example, a) reacting a compound of formula

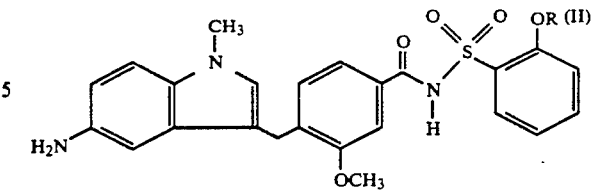

or a salt thereof with a compound of formula

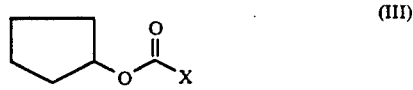

wherein X is a nucleofugal leaving group, with removal of a compound H-X, or b) in a compound of formula

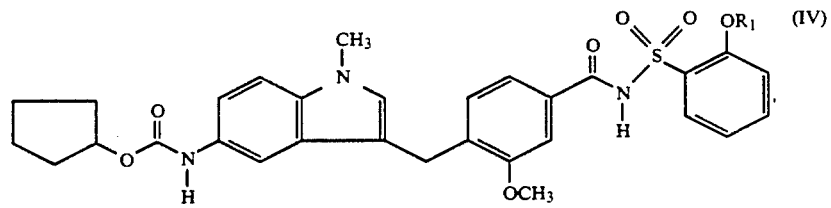

wherein R$_1$ is a group that can be converted into R, or in a salt thereof, converting R$_1$ into R, and, if desired, in each case separating a mixture of isomers obtainable in accordance with the process into the components and/or converting a free compound I obtainable in accordance with the process into a salt or converting a salt of a compound I obtainable in accordance with the process into the free compound I or into a different salt.

The reactions described hereinbefore and hereinafter are carried out in a manner known per se, for example in the absence or, usually, in the presence of a suitable solvent or diluent or a mixture thereof, the reactions being carried out, as necessary, with cooling, at room temperature or with heating, for example within a temperature range of approximately from −80° C. to the boiling point of the reaction medium, preferably from approximately −20° to approximately +150° C., and, if necessary, in a closed vessel, under pressure, in an inert gas atmosphere and/or under anhydrous conditions. Especially advantageous reaction conditions will be found in the Examples.

The starting materials mentioned hereinbefore and hereinafter which are used for the preparation of the compounds I and their salts are known, or they can be prepared by methods known per se, for example according to the procedures described hereinafter.

The comments made above with reference to salts of compounds I apply analogously to salts of starting materials mentioned hereinbefore and hereinafter.

Variant a): Nucleofugal leaving groups X in compounds III are, for example, free, etherified or esterified hydroxy or mercapto groups, sulfinyl and sulfonyl groups, and also sulfonium groups. Etherified hydroxy is, for example, lower alkoxy or unsubstituted or substituted phenyl-lower alkoxy. Esterified hydroxy is especially hydroxy esterified by a mineral acid or an organic sulfonic acid, especially halogen, sulfonyloxy and lower alkanoyloxy. Etherified mercapto is, for example, lower alkylthio, unsubstituted or substituted arylthio or unsubstituted or substituted aryl-lower alkylthio. Esterified mercapto is, for example, lower alkanoylthio. Sulfinyl is, for example, lower alkanesulfinyl, unsubstituted or substituted arylsulfinyl or unsubstituted or substituted benzylsulfinyl. Sulfonyl is, for example, lower alkanesulfonyl, unsubstituted or substituted arylsulfonyl or unsubstituted or substituted benzylsulfonyl. Sulfonium groups are, for example, di-lower alkylsulfonium groups.

The reaction of a compound II or a salt thereof with a compound III is carried out in customary manner, for example with cooling, at room temperature or with heating, in the presence or absence of an inert solvent or diluent or a mixture thereof, in the presence or absence of a basic agent and/or under inert gas.

As inert solvents or diluents there may be mentioned, for example, cyclic ethers, aromatic hydrocarbons, N,N-di-lower alkyl-lower alkanoic acid amides, phosphoric acid lower alkylamides, di-lower alkyl sulfoxides, cyclic amines, lower alkanols and, especially, unsubstituted or halogenated hydrocarbons, for example tetrahydrofuran dioxane, benzene, toluene, xylene, N,N-dimethylformamide, hexamethylphosphoric acid triamide, dimethyl sulfoxide, pyridine, N-methylmorpholine, methanol, ethanol and, especially, hexane and di- and tri-chloromethane.

Suitable basic agents are, for example, alkali metal or alkaline earth metal hydroxides, hydrides, amides, lower alkanolates, carbonates, di-lower alkylamides or lower alkylsilylamides, lower alkylamines, unsubstituted or N-lower alkylated cycloalkylamines, basic heterocycles, ammonium hydroxides and also carbocyclic amines. As examples there may be mentioned sodium hydroxide, sodium hydride, sodium amide, sodium methanolate, potassium tert-butanolate, potassium carbonate, lithium diisopropylamide, potassium bis(trimethylsilyl)amide, calcium hydride, triethylamine, cyclohexylamine, N-cyclohexyl-N,N-dimethyl-amine, pyridine, N-methylmorpholine, benzyl-trimethylammonium hydroxide and 1,5-diazabicyclo[5.4.0]undec-5-ene (DBU).

In a preferred form of variant a), a compound II is reacted at room temperature, under nitrogen or argon, in a halogenated hydrocarbon, preferably in dichloromethane, and in the presence of a basic heterocycle, preferably in the presence of N-methylmorpholine, with a compound III wherein X is halogen, preferably chlorine.

The compounds II and their salts can be prepared, for example, from the corresponding 5-nitroindole compounds by reduction of the nitro group to form the amino group. Those 5-nitroindoles in turn are obtainable, for example, by reaction of corresponding compounds that carry a carboxy group in place of the RO-benzenesulfonylaminocarbonyl group with corresponding benzenesulfonamides that are substituted in the 2-position by an RO group. The carboxy compounds in turn can be obtained, for example, by hydrolysis of corresponding carboxylic acid derivatives, for example carboxylic acid esters, while the 2-(RO)-benzenesulfonamides are obtainable, for example, by removing H-X from precursors that contain in place of the double bond in the radical R a hydrogen atom and a nucleofugal leaving group X, for example of the type mentioned above, preferably halogen, such as chlorine. More detailed information on such processes for the preparation of the starting compounds II and their precursors will be found in the Examples.

The compounds III are known, or they can be prepared analogously to the known compounds.

Variant b): Suitable groups $R_1$ are, for example, groups that are identical to the radical R except that they contain a hydrogen atom and a nucleofugal leaving group X in place of the double bond in the radical R.

Nucleofugal leaving groups X in groups $R_1$ are, for example, free, etherified or esterified hydroxy or mercapto groups, sulfinyl and sulfonyl groups, and also sulfonium groups. Etherified hydroxy is, for example, lower alkoxy or unsubstituted or substituted phenyl-lower alkoxy. Esterified hydroxy is especially hydroxy esterified by a mineral acid or an organic sulfonic acid, especially halogen, sulfonyloxy and lower alkanoyloxy. Etherified mercapto is, for example, lower alkylthio, unsubstituted or substituted arylthio or unsubstituted or substituted aryl-lower alkylthio. Esterified mercapto is, for example, lower alkanoylthio. Sulfinyl is, for example, lower alkanesulfinyl, unsubstituted or substituted arylsulfinyl or unsubstituted or substituted benzylsulfinyl. Sulfonyl is, for example, lower alkanesulfonyl, unsubstituted or substituted arylsulfonyl or unsubstituted or substituted benzylsulfonyl. Sulfonium groups are, for example, di-lower alkylsulfonium groups.

The conversion of $R_1$ into R in a compound IV or a salt thereof is effected in customary manner, for example with cooling, at room temperature or with heating, in the presence or absence of an inert solvent or diluent or a mixture thereof, in the presence or absence of a basic agent and/or under inert gas.

As inert solvents or diluents there may be mentioned, for example, cyclic ethers, aromatic hydrocarbons, N,N-di-lower alkyl-lower alkanoic acid amides, phosphoric acid lower alkylamides, di-lower alkyl sulfoxides, cyclic amines, unsubstituted or halogenated hydrocarbons and, especially, lower alkanols, for example tetrahydrofuran, dioxane, benzene, toluene, xylene, N,N-dimethylformamide, hexamethylphosphoric acid triamide, dimethyl sulfoxide, pyridine, N-methylmorpholine, hexane, di- and tri-chloromethane and, especially, methanol, ethanol and tert-butanol.

Suitable basic agents are, for example, alkali metal or alkaline earth metal hydroxides, hydrides, amides, lower alkanolates, carbonates, di-lower alkylamides or lower alkylsilylamides, lower alkylamines, unsubstituted or N-lower alkylated cycloalkylamines, basic heterocycles, ammonium hydroxides and also carbocyclic amines. As examples there may be mentioned sodium hydroxide, sodium hydride, sodium amide, sodium methanolate, potassium tert-butanolate, potassium carbonate, lithium diisopropylamide, potassium bis(trimethylsilyl)amide, calcium hydride, triethylamine, cyclohexylamine, N-cyclohexyl-N,N-dimethyl-amine, pyridine, N-methylmorpholine, benzyl-trimethylammonium hydroxide and 1,5-diazabicyclo[5.4.0]undec-5-ene (DBU).

In a preferred form of variant b), a compound IV is reacted within a temperature range of from approximately 0° to approximately +100° C. in a lower alkanol, preferably in tert-butanol, with an alkali metal lower alkanolate, preferably with potassium tert-butanolate.

The compounds IV and their salts can be obtained, for example, by reacting with a compound of formula III a 5-aminoindole compound that corresponds to a compound of formula II but carries a radical $R_1$ in place of the group R. The 5-aminoindoles can be prepared, for example, from the corresponding 5-nitroindole compounds by reduction of the nitro group to form the amino group. Those 5-nitroindoles in turn are obtainable, for example, by reaction of corresponding compounds that carry a carboxy group in place of the $R_1O$-benzenesulfonylaminocarbonyl group with corresponding benzenesulfonamides that are substituted in the 2-position by an $R_1O$ group. The carboxy compounds in turn can be obtained, for example, by hydrolysis of corresponding carboxylic acid derivatives, for example carboxylic acid esters, while the 2-($R_1O$)-benzenesulfonamides are known or can be prepared analogously to the known compounds. More detailed information on such processes for the preparation of the starting compounds IV and their precursors will be found in the Examples.

Salts of compounds I can be prepared in a manner known per se. For example, acid addition salts of compounds I are obtained, for example, by treatment with a suitable acid or a suitable ion exchange reagent, and salts with bases are obtained by treatment with a suitable base or a suitable ion exchange reagent. Salts of compounds I can be converted into the free compounds I in customary manner: acid addition salts, for example, by treatment with a suitable basic agent or a suitable ion exchange reagent, and salts with bases, for example, by treatment with a suitable acid or a suitable ion exchange reagent.

Salts of compounds I can be converted into different salts of compounds I in a manner known per se: acid addition salts, for example, can be converted into different acid addition salts, for example by treatment of a salt of an inorganic acid, such as a hydrochloride, with a suitable metal salt, such as a sodium, barium or silver salt, of an acid, for example with silver acetate, in a suitable solvent in which an inorganic salt that forms, for example silver chloride, is insoluble and therefore is eliminated from the reaction.

Depending upon the procedure and the reaction conditions, compounds I having salt-forming properties can be obtained in free form or in the form of salts.

In view of the close relationship between the compounds I in free form and in the form of their salts, hereinbefore and hereinafter any reference to the free compounds I or their salts should be understood as including the corresponding salts or free compounds I, respectively, as appropriate and expedient.

The compounds I, including the salts of salt-forming compounds, may also be obtained in the form of their hydrates and/or include other solvents, for example solvents which may have been used for crystallisation of compounds in solid form.

Depending upon the starting materials and procedures chosen, the compounds I and their salts may be in the form of one of the possible isomers or in the form of a mixture thereof. There are obtainable as pure isomers, for example, pure diastereoisomers, such as pure cis-/trans isomers. Correspondingly, there may be obtained as mixtures of isomers, for example, mixtures of diastereoisomers. Mixtures of isomers of compounds I in free form or in salt form that are obtainable in accordance with the process or by other means can be separated into the components in customary manner, for example on the basis of the physicochemical differences between the constituents by fractional crystallisation, distillation and/or chromatography in known manner. Advantageously, the more active isomer is isolated.

The invention relates also to those forms of the process according to which a compound obtainable as intermediate at any stage of the process is used as starting material and the remaining steps are carried out or a starting material is used in the form of a derivative or a salt or, especially, is formed under the reaction conditions.

In the process of the present invention there are preferably used those starting materials and intermediates, in each case in free form or in salt form, which result in the compounds I described at the beginning as being especially valuable, or their salts. The invention relates also to novel starting materials and intermediates, in each case in free form or in salt form, for the preparation of the compounds I or their salts, to the use thereof, and to processes for the preparation thereof, the variable R being as defined for the compounds I.

The invention relates also to the use of the compounds I and their pharmaceutically acceptable salts for the treatment of allergic conditions and diseases, preferably in the form of pharmaceutically acceptable compositions, especially in a method for the therapeutic treatment of the animal or human body, and to a corresponding method of treatment.

The invention relates also to pharmaceutical compositions that comprise as active ingredient a compound I or a pharmaceutically acceptable salt thereof, and to processes for their preparation. These pharmaceutical compositions are compositions for enteral, such as oral, and also rectal, administration, compositions for parenteral administration, compositions for local administration and, especially, compositions for administration by inhalation to mammals, especially humans, the compositions comprising the pharmacological active ingredient on its own or together with customary pharmaceutical excipients. The pharmaceutical preparations contain (in % by weight), for example, approximately from 0.001% to 100%, preferably from approximately 0.1% to approximately 50%, active ingredient.

Pharmaceutical preparations for enteral and parenteral administration are, for example, those in dosage unit forms, such as drages, tablets, capsules or suppositories and also ampoules. They are prepared in a manner known per se, for example by means of conventional mixing, granulating, confectioning, dissolving or lyophilising processes. For example, pharmaceutical preparations for oral administration can be obtained by combining the active ingredient with solid carriers, where appropriate granulating a resulting mixture, and processing the mixture or granulate, if desired or necessary after the addition of suitable adjuncts, into tablets or drage cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes, using, for example, corn, wheat, rice or potato starch, gelatin, tragacanth, methylcellulose and/or polyvinylpyrrolidone and, if desired, disintegrators, such as the above-mentioned starches, also carboxymethyl starch, cross-linked polyvinylpyrrolidone, agar or alginic acid or a salt thereof, such as sodium alginate. Adjuncts are especially flow-regulating agents and lubricants, for example silicic acid, talc, stearic acid or salts thereof, such as magnesium or calcium stearate, and/or polyethylene glycol. Drage cores are provided with suitable coatings that may be resistant to gastric juices, there being used, inter alia, concentrated sugar solutions that optionally contain gum arabic, talc, polyvinylpyrrolidone, polyethylene glycol and/or titanium dioxide, or lacquer solutions in suitable organic solvents or solvent mixtures or, to produce coatings that are resistant to gastric juices, solutions of suitable cellulose preparations, such as acetylcellulose phthalate or hydroxypropylmethylcellulose phthalate. Colouring substances or pigments may be added to the tablets or drage coatings, for example for the purpose of identification or to indicate different doses of active ingredient.

Other orally administrable pharmaceutical preparations are dry-filled capsules made of gelatin, and also soft, sealed capsules made of gelatin and a plasticiser, such as glycerol or sorbitol. The dry-filled capsules may contain the active ingredient in the form of a granulate, for example in admixture with fillers, such as lactose, binders, such as starches, and/or glidants, such as talc or magnesium stearate, and, where appropriate, stabilisers. In soft capsules the active ingredient is preferably dissolved or suspended in suitable liquids, such as fatty oils, paraffin oil or liquid polyethylene glycols, it being possible also for stabilisers to be added.

Suitable rectally administrable pharmaceutical preparations are, for example, suppositories that consist of a combination of the active ingredient with a suppository base material.

Suitable suppository base materials are, for example, natural or synthetic triglycerides, paraffin hydrocarbons, polyethylene glycols or higher alkanols. It is also possible to use gelatin rectal capsules that contain a combination of the active ingredient with a base material. Suitable base materials are, for example, liquid triglycerides, polyethylene glycols or paraffin hydrocarbons.

There are suitable for parenteral administration especially aqueous solutions of an active ingredient in water-soluble form, for example in the form of a water-soluble salt, and also suspensions of the active ingredient, such as corresponding oily injection suspensions, for which suitable lipophilic solvents or vehicles, such as fatty oils, for example sesame oil, or synthetic fatty acid esters, for example ethyl oleate or triglycerides, are used, or aqueous injection suspensions that contain viscosity-increasing substances, for example sodium carboxymethylcellulose, sorbitol and/or dextran, and, where appropriate, also stabilisers.

Pharmaceutical compositions for local administration are, for example, for the topical treatment of the skin, lotions, creams and ointments, that is to say liquid or semi-solid oil-in-water or water-in-oil emulsions, fatty ointments which are anhydrous, pastes, that is to say creams and ointments with secretion-absorbing powder constituents, gels which are aqueous, of low water-content or anhydrous and consist of swellable, gel-forming materials, foams, that is to say liquid oil-in-water emulsions in aerosol form which are administered from pressurised containers, and tinctures which have an aqueous-ethanolic base, it being possible that these compositions in each case contain other customary pharmaceutical excipients, such as preservatives. Suitable for the local treatment of the eyes are, for example, eye drops which comprise the active ingredient in sterile aqueous or oily solution, and eye ointments which are also preferably manufactured in sterile form. Suitable for the local treatment of the nose are, for example, sprays, similar to those described below for the treatment of the respiratory tract, coarse powders which are administered by rapid inhalation through the nostrils, and especially nose drops which comprise the active ingredient in aqueous or oily solution. Suitable for the local treatment of the buccal cavity are, for example, lozenges and pastilles which comprise the active ingredient in an inert mass formed, for example, of sugar and gum arabic or tragacanth, to which flavourings may be added. The pharmaceutical compositions for local administration are prepared in a manner known per se by mixing the active ingredient with the pharmaceutical excipients, for example by dissolving or suspending the active ingredient in the base material or in a portion thereof, if necessary. In order to prepare emulsions in which the active ingredient is dissolved in one of the liquid phases, the active ingredient is, as a rule, dissolved therein before the emulsification; in order to prepare suspensions in which the active ingredient is suspended in the emulsion, the active ingredient is mixed with a portion of the base material after the emulsification and then added to the remainder of the formulation.

Pharmaceutical compositions for administration by inhalation are compositions in which the active ingredient is present in micronised form, that is to say compositions in which the particle size of the active ingredient is less than 20 $\mu$m, especially less than 10 $\mu$m and advantageously less than 5 $\mu$m, for example micronised powders and aerosols which are administered in the form of sprays. The micronised powders comprise the active ingredient on its own or in admixture with an inert carrier, such as lactose, advantageously together with one of the propellants mentioned hereinafter. Aerosols are solutions, suspensions or emulsions of the active ingredient in a suitable, pharmaceutically acceptable liquid phase, such as in ethanol or water or a corresponding mixture, which may, as necessary, also comprise other pharmaceutical excipients, such as non-ionic or anionic surface-active agents, emulsifiers and stabilisers, and/or active ingredients of other kinds, and which comprise a propellant, for example an inert gas, such as butane, under elevated pressure or especially a readily volatile liquid, preferably a liquid that boils under normal pressure below customary room temperature (for example at from approximately $-30°$ C. to approximately $+10°$ C.), such as an at least partially fluorinated polyhalogenated lower alkane, or a mixture of such liquids. For the preparation of the pharmaceutical compositions in dosage forms finished for administration by inhalation, a corresponding pharmaceutical composition is introduced, together with the propellant, into suitable containers, such as flacons or pressurised bottles, which are provided with a suitable spray device, for example a valve. The valve is preferably constructed in the form of a metering valve which on operation releases a predetermined amount of the contents of the container, corresponding to a predetermined dose of the active ingredient. In the preparation of the finished pharmaceutical dosage form, it is also possible for appropriate amounts of the pharmaceutical composition and of the propellant to be introduced separately into the containers and to be mixed with one another only at that stage.

The dosage of the active ingredient may depend on various factors, such as effectiveness and duration of action of the active ingredient, severity of the disease to be treated and its symptoms, respectively, mode of administration, warm-blooded species, and/or sex, age, weight and individual condition of the warm-blooded animal. The approximate daily dosage normally to be recommended for a warm-blooded animal weighing approximately 75 kg is from approximately 10 mg to approximately 1500 mg, especially from approximately 25 to approximately 250 mg, which is optionally taken in several, optionally equal, partial doses.

The following Examples illustrate the invention described hereinbefore, but do not limit the scope thereof in any way. Temperatures are given in degrees Celsius. "DMSO" means dimethyl sulfoxide.

EXAMPLE 1

A solution of 1.15 g of cyclopentyl chloroformate in 20 ml of dichloromethane is added to a solution of 3.99 g of 2-vinyloxybenzenesulfonic acid N-[4-(5-amino-1-methyl-indol-3-ylmethyl)-3-methoxy-benzoyl]amide in 30 ml of dichloromethane and 2.3 g of N-methylmorpholine. The mixture is stirred at room temperature for two hours with the introduction of nitrogen and is then poured onto a mixture of 40 g of ice and 20 ml of 1N hydrochloric acid. The organic phase is separated off, washed in succession with 20 ml of saturated sodium chloride solution and 20 ml of water, dried over magnesium sulfate and concentrated by evaporation under 11 Torr at 40°. The residue is chromatographed by means of MPLC on 300 g of silica gel (Merck, Lichroprep Si 60/25–40 μm). Fractions 1–4, eluted with dichloromethane, are discarded. Fractions 5–12, eluted with dichloromethane, are combined and concentrated by evaporation under 11 Torr at 40°. The residue is dissolved in approximately 10 ml of dichloromethane, and petroleum ether is added to the solution until the solution starts to turn cloudy. The crystals which have separated out are filtered off and then washed with dichloromethane/petroleum ether (1:1) and dried under 0.01 Torr at 60°. The 2-vinyloxybenzenesulfonic acid N-[4-(5-cyclopentyloxycarbonylamino-1-methyl-indol-3-ylmethyl)-3-methoxy-benzoyl]amide (i.e. the compound of formula I wherein R is vinyl) melts at 161°–165°.

The starting material can be prepared, for example, as follows:

a) 10.0 g of 3-methoxy-4-(1-methyl-5-nitro-indol-3-ylmethyl)-benzoic acid methyl ester are dissolved in 240 ml of tetrahydrofuran and 180 ml of methanol. To that solution there is added a solution of 4.2 g of lithium hydroxide (monohydrate) in 70 ml of water. The mixture is stirred at room temperature for 15 hours and concentrated to a volume of approximately 50 ml under 11 Torr at 50°. The residue is diluted with 50 ml of water, and the mixture is acidified with 1N hydrochloric acid. The yellow crystals which have separated out are filtered off, washed with 20 ml of water and dried under 0.01 Torr at 40° for 20 hours. The 3-methoxy-4-(1-methyl-5-nitro-indol-3-ylmethyl)-benzoic acid melts at 263°–265°.

b) A solution of 4.0 g of 3-methoxy-4-(1-methyl-5-nitro-indol-3-ylmethyl)-benzoic acid in 200 ml of tetrahydrofuran is added at room temperature, with stirring and with the introduction of argon, to a mixture of 2.72 g of N-(3-dimethylaminopropyl)-N'-ethylcarbodiimide hydrochloride, 2.72 g of 2-vinyloxybenzenesulfonic acid amide and 1.72 g of 4-dimethylaminopyridine in 120 ml of dichloromethane. The mixture is stirred for 5 hours at 42° and then for 15 hours at room temperature. The yellow crystals which have separated out are filtered off and dissolved in 300 ml of trichloromethane/methanol (9:1), and the solution is chromatographed on 600 g of silica gel. Fractions 1–5, each eluted with 300 ml of trichloromethane/methanol (9:1), are combined and concentrated by evaporation under 11 Torr at 40°. The residue is stirred with diethyl ether, whereupon 2-vinyloxybenzenesulfonic acid N-[4-(1-methyl-5-nitro-indol-3-ylmethyl)-3-methoxy-benzoyl]amide crystallises out (yellow crystals; m.p.: 165°–170°).

c) To a solution of 2.0 g of 2-vinyloxybenzenesulfonic acid N-[4-(1-methyl-5-nitro-indol-3-ylmethyl)-3-methoxy-benzoyl]amide in 40 ml of dimethyl sulfoxide there are added 1.0 g of Lindlar catalyst [palladium on calcium carbonate (5%), contaminated with lead] and 10 mg of 1,8-dihydroxy-3,6-dithia-octane, and the mixture is then hydrogenated for 20 hours at 20°–22° under normal pressure. In order to remove the catalyst, the mixture is filtered through Hyflo Super Cel. The filtrate is concentrated by evaporation under 0.01 Torr at 30°. The residue is chromatographed on 300 g of silica gel. Fractions 1–3, each eluted with 100 ml of ethyl acetate, are discarded. Fractions 4–15, each eluted with 100 ml of ethyl acetate/methanol (9:1), are combined and concentrated by evaporation under 11 Torr at 40°. The residue is stirred with diethyl ether, whereupon 2-vinyloxybenzenesulfonic acid N-[4-(5-amino-1-methyl-indol-3-ylmethyl)-3-methoxy-benzoyl]amide crystallises out [pink crystals, m.p.: 145°–150°, $^1$H-NMR (DMSO-$d_6$, 400 MHz): 7.87 (d, d, 1H), 7.49 (m, 2H), 7.34 (d, d, 1H), 7.16 (t, 1H), 7.09 (m, 2H), 6.95 (d, 1H), 6.88 (s, 1H), 6.71 (d, d, 1H), 6.64 (d, 1H), 6.57 (d, d, 1H), 4.67 (d, d, 1H), 4.42 (d, d, 1H), 3.84 (s, 5H), 3.61 (s, 3H)].

d) 23.14 g of potassium tert-butanolate are added in portions at room temperature, with stirring, to a suspension of 11.8 g of 2-(2-chloroethoxy)benzenesulfonic acid amide in 150 ml of tert-butanol. The mixture is stirred for 4 hours at 80°, cooled and concentrated by evaporation under 11 Torr at 40°. The residue is dissolved in approximately 100 ml of ice-water, the solution is adjusted to pH 7 with concentrated hydrochloric acid, and the white crystals are filtered off and dried for 15 hours under 11 Torr at 70°. The 2-vinyloxybenzenesulfonic acid amide melts at 140°–142°.

EXAMPLE 2

0.72 g of potassium tert-butanolate is added at room temperature, with stirring, to a suspension of 1.0 g of 2-(2-chloroethoxy)benzenesulfonic acid N-[4-(5-cyclopentyloxycarbonylamino-1-methyl-indol-3-ylmethyl)-3-methoxy-benzoyl]amide in 4.7 ml of tert-butanol. The mixture is stirred at 80° for one hour and poured onto a mixture of 30 ml of ice-water and 3 ml of 2N hydrochloric acid. The suspension is extracted twice with 50 ml of ethyl acetate each time. The combined organic phases are washed in succession with 20 ml of saturated sodium hydrogen carbonate solution and twice with 20 ml of brine each time, dried over magnesium sulfate and concentrated by evaporation under 11 Torr at 40°. The residue is chromatographed by means of MPLC on 80 g of silica gel (Merck, Lichroprep Si 60/25–40 μm). Fractions 1–5, eluted with dichloromethane, are discarded. Fractions 6–12, eluted with dichloromethane, are combined and concentrated by evaporation under 11 Torr at 40°. The residue is crystallised from dichloromethane/petroleum ether. The 2-vinyloxybenzenesulfonic acid N-[4-(5-cyclopentyloxycarbonylamino-1-methyl-indol-3-ylmethyl)-3-methoxy-benzoyl]amide melts at 161°–165°.

The starting material can be prepared, for example, as follows:

a) Analogously to Example 1b) the 2-(2-chloroethoxy)benzenesulfonic acid N-[4-(1-methyl-5-nitro-indol-3-ylmethyl)-3-methoxy-benzoyl]amide is obtained [yellow powder, m.p.: 150°–160° (after trituration with diethyl ether), $^1$H-NMR (DMSO-$d_6$, 360 MHz): 8.48 (d, 1H), 8.00 (d, d, 1H), 7.90 (d, d, 1H), 7.59 (d, 1H), 7.54 (d, 1H), 7.46 (d, d, 1H), 7.43 (t, d, 1H), 7.26 (s, 1H), 7.15 (d, 1H), 7.06 (t, d, 1H), 4.29 (t, 2H), 4.08 (s, 2H), 3.89 (s, 3H), 3.80 (m, 5H)].

b) To a solution of 1.05 g of 2-(2-chloroethoxy)benzenesulfonic acid N-[4-(1-methyl-5-nitro-indol-3-ylmethyl)-3-methoxy-benzoyl]amide in 45 ml of tetrahydrofuran there is added 0.3 g of Rh/C catalyst (5%), and the mixture is then hydrogenated for 20 hours at 20°–22° under normal pressure, a further 0.1 g of Rh/C catalyst (5%) being added after 10 hours' hydrogenation. In order to remove the catalyst, the mixture is filtered through Hyflo Super Cel. The filtrate is concentrated to dryness by evaporation under 11 Torr at 40°. The residue is flash-chromatographed on 35 g of silica gel. Fractions 1–9, each eluted with 50 ml of ethyl acetate, are discarded. Fractions 10–13, each eluted with 50 ml of ethyl acetate, are combined and concentrated by evaporation under 11 Torr at 40°. The residue is crystallised from ethyl acetate/diethyl ether. The 2-(2-chloroethoxy)benzenesulfonic acid N-[4-(5-amino-1-methyl-indol-3-ylmethyl)-3-methoxy-benzoyl]amide (beige crystals) melts at 300° with decomposition [$^1$H-NMR (DMSO-$d_6$, 400 MHz): 7.85 (d, d, 1H), 7.53 (d, 1H), 7.46 (t, 1H), 7.38 (d, d, 1H), 7.10 (m, 3H), 6.98 (d, 1H), 6.83 (s, 1H), 6.60 (d, 1H), 6.54 (d, d, 1H), 4.26 (t, 2H), 3.86 (s, 3H), 3.85 (s, 2H), 3.82 (t, 2H), 3.60 (s, 3H)].

c) Analogously to Example 1 the 2-(2-chloroethoxy)-benzenesulfonic acid N-[4-(5-cyclopentyloxycarbonylamino-1-methyl-indol-3-ylmethyl)-3-methoxy-benzoyl]amide is obtained [pink crystals, m.p.: 168°–171° (from dichloromethane/petroleum ether), $^1$H-NMR (CDCl$_3$, 400 MHz): 9.04 (s, 1H), 8.21 (d, d, 1H), 7.60 (m, 1H), 7.52 (m, 1H), 7.35 (d, 1H), 7.27 (d, 1H), 7.20 (m, 3H), 7.12 (d, 1H), 6.95 (d, 1H), 6.77 (s, 1H), 6.52 (s, 1H), 5.20 (m, 1H), 4.31 (t, 2H), 4.05 (s, 2H), 3.87 (s, 3H), 3.85 (t, 2H), 3.72 (s, 3H)].

EXAMPLE 3

A solution of 0.9 g of cyclopentyl chloroformate in 15 ml of dichloromethane is added to a solution of 2.98 g of (Z)-2-propen-1-yloxybenzenesulfonic acid N-[4-(5-amino-1-methyl-indol-3-ylmethyl)-3-methoxy-benzoyl]amide in 80 ml of dichloromethane and 1.79 g of N-methylmorpholine. The mixture is stirred at room temperature for two hours under an argon atmosphere and then poured onto a mixture of 30 g of ice and 30 ml of 1N hydrochloric acid. The organic phase is separated off, washed in succession with 20 ml of saturated sodium chloride solution and 20 ml of water, dried over magnesium sulfate and concentrated by evaporation under 11 Torr at 40°. The residue is chromatographed by means of MPLC on 250 g of silica gel (Merck, Lichroprep Si 60/25-40 μm). Fractions 1–3, eluted with dichloromethane, are discarded. Fractions 4–6, eluted with dichloromethane, are combined and concentrated by evaporation under 11 Torr at 40°. The residue is stirred with diethyl ether/petroleum ether, and the white crystals are filtered off. The (Z)-2-propen-1-yloxybenzenesulfonic acid N-[4-(5-cyclopentyloxycarbonylamino-1-methyl-indol-3-ylmethyl)-3-methoxy-benzoyl]amide melts at 181°–183° [$^1$H-NMR (CDCl$_3$, 400 MHz): 8.19 (d, d, 1H), 7.55 (t, d, 1H), 7.52 (m, 1H), 7.34 (d, 1H), 7.28–7.08 (m, 5H), 7.04 (d, d, 1H), 6.76 (s, 1H), 6.30 [d, q, 1H; $^3J_{(OCH=CH)} = 6$ Hz], 5.20 (m, 1H), 5.07 [m, 1H; $^3J_{(OCH=CH)} = 6$ Hz], 4.05 (s, 2H), 3.86 (s, 3H), 3.72 (s, 3H), 2.0–1.55 (m, 8H), 1.58 (d, d, 3H)].

The following can be prepared analogously:

(E)-2-propen-1-yloxybenzenesulfonic acid N-[4-(5-cyclopentyloxycarbonylamino-1-methyl-indol-3-ylmethyl)-3-methoxy-benzoyl]amide [m.p.: 202°–205° (from dichloromethane/petroleum ether), $^1$H-NMR (CDCl$_3$, 400 MHz): 8.96 (s, 1H), 8.20 (d, d, 1H), 7.59 (m, 2H), 7.35 (d, 1H), 7.26–7.13 (m, 5H), 7.08 (d, 1H), 6.80 (s, 1H), 6.49 (s, 1H), 6.34 [d, q, 1H; $^3J_{(OCH=CH)} = 12$ Hz], 5.45 [d, q, 1H; $^3J_{(OCH=CH)} = 12$ Hz], 5.21 (m, 1H), 4.07 (s, 2H), 3.88 (s, 3H), 3.74 (s, 3H), 1.95–1.58 (m, 8H), 1.60 (d, d, 3H)].

The starting materials can be prepared, for example, as follows:

a) A hot solution of 2.0 g of 3-methoxy-4-(1-methyl-5-nitro-indol-3-ylmethyl)-benzoic acid in 100 ml of tetrahydrofuran is added at room temperature, with stirring and with the introduction of argon, to a solution of 1.18 g of N-(3-dimethylaminopropyl)-N'-ethylcarbodiimide hydrochloride, 1.26 g of (Z)-2-propen-1-yloxybenzenesulfonic acid amide and 0.74 g of 4-dimethylaminopyridine in 60 ml of dichloromethane. The yellow solution is stirred at room temperature for 12 hours, crystallisation beginning after only 5 minutes. The yellow crystals are filtered off and washed with 10 ml of dichloromethane. The (Z)-2-propen-1-yloxybenzenesulfonic acid N-[4-(1-methyl-5-nitro-indol-3-ylmethyl)-3-methoxy-benzoyl]amide melts at 180°–185°.

The following can be prepared analogously:

(E)-2-propen-1-yloxybenzenesulfonic acid N-[4-(1-methyl-5-nitro-indol-3-ylmethyl)-3-methoxy-benzoyl]amide [m.p.: 210°–215° (from tetrahydrofuran/dichloromethane)].

b) To a solution of 1.0 g of (Z)-2-propen-1-yloxybenzenesulfonic acid N-[4-(1-methyl-5-nitro-indol-3-ylmethyl)-3-methoxy-benzoyl]amide in 50 ml of dimethyl sulfoxide there are added 1.0 g of Lindlar catalyst and 5 mg of 1,8-dihydroxy-3,6-dithiaoctane, and the mixture is then hydrogenated at 20°–22° under normal pressure until the reaction ceases (7 hours). In order to remove the catalyst, the mixture is filtered through Hyflo Super Cel. The filtrate is concentrated by evaporation under 0.01 Torr at 30°. The residue is chromatographed on 80 g of silica gel. Fractions 1–5, each eluted with 60 ml of ethyl acetate, are discarded. Fractions 6–13, eluted with the same solvent, are combined and concentrated by evaporation under 11 Torr at 40°. The residue is stirred with diethyl ether, whereupon the (Z)-2-propen-1-yloxybenzenesulfonic acid N-[4-(5-amino-1-methyl-indol-3-ylmethyl)-3-methoxy-benzoyl]amide crystallises out [yellowish crystals, m.p.: 135°–140°, $^1$H-NMR (DMSO-d$_6$, 400 MHz): 7.88 (d, d, 1H), 7.54 (d, 1H), 7.44 (t, d, 1H), 7.37 (d, d, 1H), 7.10 (t, d, 1H), 7.06 (d, 1H), 7.02 (d, d, 1H), 6.99 (d, 1H), 6.81 (s, 1H), 6.63 (d, 1H), 6.56 (d, d, 1H), 6.47 [m, 1H; $^3J_{(OCH=CH)}$=6 Hz], 4.88 [m, 1H; $^3J_{(OCH=CH)}$=6 Hz], 3.86 (s, 2H), 3.84 (s, 3H), 3.60 (s, 3H), 1.56 (d, d, 3H)].

The following can be prepared analogously:

(E)-2-propen-1-yloxybenzenesulfonic acid N-[4-(5-amino-1-methyl-indol-3-ylmethyl)-3-methoxy-benzoyl]amide [m.p.: 140°–145° (after trituration with diethyl ether), $^1$H-NMR (400 MHz, DMSO-d$_6$, 60°): 7.90 (d, d, 1H), 7.52 (m, 2H), 7.37 (d, d, 1H), 7.16 (t, d, 1H), 7.12 (d, d, 1H), 7.08 (d, 1H), 7.03 (d, 1H), 6.85 (s, 1H), 6.66 (d, 1H), 6.58 (d, d, 1H), 6.54 [q, d, 1H; $^3J_{(OCH=CH)}$=12 Hz], 5.27 [q, d, 1H; $^3J_{(OCH=CH)}$=12 Hz], 3.87 (s, 5H), 3.61 (s, 3H), 1.52 (d, d, 3H)].

c) 14.6 g of potassium tert-butanolate are added over a period of 5 minutes, with stirring, to a solution of 21.3 g of 2-allyloxybenzenesulfonic acid amide in 100 ml of dimethyl sulfoxide, the temperature being kept below 30° by cooling. The mixture is stirred at room temperature for 15 hours. The resulting suspension is poured onto 300 ml of water and the mixture is adjusted to pH 7 with 2N hydrochloric acid. The suspension is stirred at 10°–15° for 15 minutes and then filtered. The white crystals (filter cake) are washed with 50 ml of water and dried for 15 hours under 0.1 Torr at 40°. The (Z)-2-propen-1-yloxybenzenesulfonic acid amide melts at 106°–107° [$^1$H-NMR (CDCl$_3$, 400 MHz): $^3J_{Olefin}$=5.9 Hz].

d) 4.2 g of potassium tert-butanolate are added, with stirring, to a solution of 2.5 g of 2-(2-chloropropyloxy)benzenesulfonic acid amide in 27 ml of tert-butanol. The mixture is stirred at an internal temperature of 80° and cooled, and a mixture of 25 ml of ice-water and 5 ml of concentrated hydrochloric acid is added to the white suspension. The mixture is extracted three times with 70 ml of ethyl acetate each time and the combined organic phases are washed in succession with 40 ml of 2N sodium hydrogen carbonate solution and three times with 40 ml of saturated sodium chloride solution each time, dried over magnesium sulfate and concentrated to dryness under 11 Torr at 40°. The crystalline residue is stirred with 50 ml of diethyl ether, and the crystals are filtered off. The (E)-2-propen-1-yloxybenzenesulfonic acid amid melts at 145°–146° [$^1$H-NMR (400 MHz, CDCl$_3$): $^3J_{Olefin}$=12.4 Hz].

e) A solution of 8.64 ml of bromoacetone (70%) in 10 ml of anhydrous N,N-dimethylformamide is added, with stirring and with cooling, to a mixture of 10.38 g of 2-hydroxybenzenesulfonic acid amide, 16.6 g of potassium carbonate and 1.0 g of potassium iodide in 45 ml of anhydrous N,N-dimethylformamide. The suspension is stirred at room temperature for one hour and then poured onto a mixture of 100 ml of ice-water and 15 ml of concentrated hydrochloric acid. The mixture is extracted four times with 50 ml of ethyl acetate each time. The combined organic extracts are washed four times with 25 ml of saturated sodium chloride solution each time, dried over magnesium sulfate and concentrated under 11 Torr at 40°, whereupon 2-(2-oxopropyloxy)benzenesulfonic acid amide crystallises out (m.p.: 158°–159°).

f) 1.0 g of sodium borohydride is added in portions, with stirring and with cooling, to a suspension of 11.5 g of 2-(2-oxopropyloxy)benzenesulfonic acid amide in 50 ml of ethanol and 6 ml of water. The suspension is stirred at room temperature for 4 hours, 5 ml of acetone are added, and the mixture is concentrated to dryness under 11 Torr at 50°. 150 ml of ethyl acetate and 50 ml of water are added to the residue. The pH of the mixture is adjusted to 2–3 by the addition of 2N hydrochloric acid. The organic phase is separated off, washed in succession twice with 50 ml of water each time and twice with 50 ml of saturated sodium chloride solution each time, dried over sodium sulfate and concentrated to dryness under 11 Torr. The residue is crystallised from acetone/diethyl ether. The 2-(2-hydroxypropyloxy)benzenesulfonic acid amide melts at 110°–111°.

g) 9.0 ml of 1-chloro-1-(N,N-dimethylamino)-2-methyl-propene are added at 25°, with stirring, to a suspension of 11.6 g of 2-(2-hydroxypropyloxy)-benzenesulfonic acid amide in 300 ml of trichloromethane. The mixture is stirred at 25° for 30 minutes, diluted with 200 ml of trichloromethane and poured onto 1000 ml of ice-water. The organic phase is separated off, washed twice with 100 ml of water each time, dried over sodium sulfate and concentrated under 11 Torr at 40°. The residue is subjected to flash chromatography on 600 g of silica gel with toluene/ethyl acetate (4:1). The eluate is concentrated under 11 Torr at 50°. The residue is triturated with diethyl ether, and the crystals are filtered off. The 2-(2-chloropropyloxy)benzenesulfonic acid amide melts at 113°–114°.

EXAMPLES A THROUGH H

Pharmaceutical Compositions

In the following, the term "active ingredient" is to be understood as being a compound I, in free form or in form of a pharmaceutically acceptable salt, especially a compound I described as a product in the Examples 1 to 3, for example the 2-vinyloxybenzenesulfonic acid N-[4-(5-cyclopentyloxycarbonylamino-1-methyl-indol-3-ylmethyl)-3-methoxy-benzoyl]amide.

EXAMPLE A

An inhalation suspension, containing propellant and forming a solid aerosol, comprising 0.1% by weight of active ingredient.

| Composition | % by weight |
|---|---|
| active ingredient, micronised | 0.1 |
| sorbitan trioleate | 0.5 |
| propellant A (trichlorotrifluoroethane) | 4.4 |
| propellant B (dichlorodifluoromethane and 1,2-dichlorotetrafluoroethane) | 15.0 80.0 |

In the absence of moisture, the active ingredient is suspended in the trichlorotrifluoroethane using a customary homogeniser, with the addition of the sorbitan trioleate, and the suspension is introduced into an aerosol container provided with a metering valve. The container is sealed and filled up with propellant B under pressure.

EXAMPLE B

An approximately 2% aqueous solution, suitable for inhalation, of the active ingredient in the form of its sodium or potassium salt.

| Composition | |
|---|---|
| active ingredient (potassium or sodium salt) | 2000 mg |
| disodium salt of ethylenediaminetetraacetic acid | 10 mg |
| benzalkonium chloride | 10 mg |
| water, freshly distilled | ad 100 ml |
| propellant | as required |

The active ingredient is dissolved in approximately 60 ml of freshly distilled water, and the stabiliser (disodium salt of ethylenediaminetetraacetic acid) and the preservative (benzalkonium chloride) are added. When all the components have completely dissolved, the resulting solution is made up to 100 ml and introduced into small pressurised bottles. The small bottles are sealed in gas-tight manner. The propellant is added, as required, in gaseous form under pressure or in liquid form.

EXAMPLE C

An ointment comprising 0.05% by weight of active ingredient.

| Composition | % by weight |
|---|---|
| active ingredient | 0.05 |
| vaseline | 45.00 |
| paraffin oil | 19.60 |
| cetyl alcohol | 5.00 |
| beeswax | 5.00 |
| sorbitan sesquioleate | 5.00 |
| p-hydroxybenzoic acid ester | 0.20 |
| water, demineralised | 20.15 |

The fatty substances and emulsifiers are melted together. The preservative is dissolved in water, and the solution is emulsified in the fatty melt at elevated temperature. After cooling, a suspension of the active ingredient in a portion of the fatty melt is incorporated into the emulsion.

EXAMPLE D

Eye drops comprising 0.3% by weight of active ingredient.

| Composition (10,000 bottles at 10 ml each) | % by weight |
|---|---|
| active ingredient | 0.30 |
| disodium phosphate | 0.31 |
| citric acid | 0.15 |
| sodium chloride | 0.35 |
| sodium pyrosulphite | 0.10 |
| benzalkonium chloride | 0.01 |
| water, demineralised | 98.78 |

The active ingredient and all the additives mentioned are stirred into 80 liters of demineralised water under a nitrogen atmosphere. When all the ingredients have dissolved completely, the solution is made up to 100 liters with demineralised water, sterilised in an autoclave at 120° for 20 minutes and then filtered under sterile conditions through a membrane filter (pore diameter: 0.2 μm). Every 10 ml of the filtrate is introduced under aseptic conditions into a bottle having a dropping pipette closure.

EXAMPLE E

Tablets, each comprising 50 mg of active ingredient.

| Composition (10,000 tablets) | |
|---|---|
| active ingredient | 500.0 g |
| lactose | 500.0 g |
| potato starch | 352.0 g |
| gelatin | 8.0 g |
| talc | 60.0 g |
| magnesium stearate | 10.0 g |
| silica (highly disperse) | 20.0 g |
| ethanol | q.s. |

The active ingredient is mixed with the lactose and 292 g of the potato starch, and the mixture is moistened with an ethanolic solution of the gelatin and granulated through a sieve. After drying, the remainder of the potato starch, the magnesium stearate, the talc and the silica are admixed and the mixture is compressed to give tablets each of weight 145 mg and active ingredient content 50 mg, which, if desired, can be provided with breaking notches for finer adjustment of the dosage.

EXAMPLE F

Film-coated tablets, each comprising 100 mg of active ingredient.

| Composition (1000 film-coated tablets) | |
|---|---|
| active ingredient | 100.0 g |
| lactose | 100.0 g |
| cornflour | 70.0 g |
| talc | 8.5 g |
| calcium stearate | 1.5 g |
| hydroxypropylmethylcellulose | 2.36 g |
| shellac | 0.64 g |
| water | q.s. |
| dichloromethane | q.s. |

The active ingredient, the lactose and 40 g of the cornflour are mixed. The mixture is moistened with a paste, prepared from 15 g of cornflour and water (with warming), and is granulated. The granules are dried, and the remainder of the cornflour, the talc and the calcium stearate are mixed with the granules. The mixture is compressed to give tablets (weight: 280 mg each) and these are coated with a solution of the hydroxypropylmethylcellulose and the shellac in dichloromethane (final weight of the film-coated tablets: 283 mg each).

EXAMPLE G

Hard gelatin capsules, each comprising 100 mg of active ingredient.

| Composition (1000 capsules) | |
|---|---|
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is sieved into the lyophilised active ingredient through a sieve having a mesh width of 0.2 mm. Both components are intimately mixed. The lactose is then first sieved in through a sieve having a mesh width of 0.6 mm and subsequently the microcrystalline cellulose through a sieve having a mesh width of 0.9 mm. The four components are then intimately mixed for 10 minutes. Finally, the magnesium stearate is sieved in through a sieve having a mesh width of 0.8 mm. After further mixing (3 minutes), 390 mg each of the formulation obtained is filled into hard gelatin capsules of size 0.

EXAMPLE H

An injection or infusion solution, comprising 5 mg of active ingredient per ampoule at 2.5 ml each.

| Composition (1000 ampoules) | |
| --- | --- |
| active ingredient | 5.0 g |
| sodium chloride | 22.5 g |
| phosphate buffer solution (pH: 7.4) | 300.0 g |
| demineralised water | ad 2500.0 ml |

The active ingredient and the sodium chloride are dissolved in 1000 ml of demineralised water. The solution is filtered through a microfilter. The filtrate is treated with the phosphate buffer solution, and the mixture is made up to 2500 ml with demineralised water. To prepare unit dose forms, 2.5 ml of the mixture each time are filled into glass ampoules, which then each contain 5 mg of active ingredient.

What is claimed is:

1. A compound of the formula

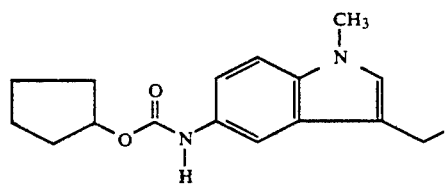

(I)

-continued

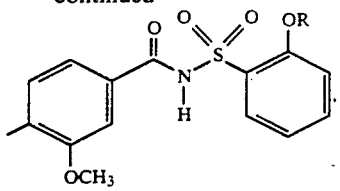

wherein R is straight-chain $C_2-C_4$alk-1-en-1-yl, in free form or in form of a pharmaceutically acceptable salt.

2. A compound according to claim 1 of the formula I, in which R is vinyl, (Z)-propen-1-yl or (E)-propen-1-yl, in free form or in form of a pharmaceutically acceptable salt.

3. A compound according to claim 1 of the formula I, in which R is vinyl or (Z)-propen-1-yl, in free form or in form of a pharmaceutically acceptable salt.

4. A compound as claimed in claim 1 being 2-vinyloxybenzenesulfonic acid N-[4-(5-cyclopentyloxycarbonylamino-1-methyl-indol-3-ylmethyl)-3-methoxy-benzoyl]amide, in free form or in form of a pharmaceutically acceptable salt.

5. A compound as claimed in claim 1 being (Z)-2-propen-1-yloxybenzenesulfonic acid N-[4-(5-cyclopentyloxycarbonylamino-1-methyl-indol-3-ylmethyl)-3-methoxy-benzoyl]amide, in free form or in form of a pharmaceutically acceptable salt.

6. A compound as claimed in claim 1 being (E)-2-propen-1-yloxybenzenesulfonic acid N-[4-(5-cyclopentyloxycarbonylamino-1-methyl-indol-3-ylmethyl)-3-methoxy-benzoyl]amide, in free form or in form of a pharmaceutically acceptable salt.

7. A pharmaceutically composition comprising an antiallergically effective amount of a compound according to claim 1 in free form or in the form of a pharmaceutically acceptable salt, if appropriate in addition to customary pharmaceutical adjuncts.

8. A method of treating allergic conditions and diseases in a subject in need of such treatment, which method comprises administering to such subject an antiallergically effective amount of a compound according to claim 1 in free form or in the form of a pharmaceutically acceptable salt.

* * * * *